(12) United States Patent
Huang et al.

(10) Patent No.: US 7,875,233 B2
(45) Date of Patent: Jan. 25, 2011

(54) METHOD OF FABRICATING A BIAXIALLY ORIENTED IMPLANTABLE MEDICAL DEVICE

(75) Inventors: Bin Huang, Pleasanton, CA (US); David C. Gale, San Jose, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 1075 days.

(21) Appl. No.: 11/184,130

(22) Filed: Jul. 18, 2005

(65) Prior Publication Data

US 2006/0076708 A1  Apr. 13, 2006

Related U.S. Application Data

(63) Continuation-in-part of application No. 10/956,910, filed on Sep. 30, 2004.

(51) Int. Cl.
*B29C 49/64* (2006.01)
*B29C 49/08* (2006.01)
*B29C 49/20* (2006.01)

(52) U.S. Cl. .............. 264/512; 264/516; 264/573; 264/241

(58) Field of Classification Search .......... 264/573, 264/291, 482
See application file for complete search history.

(56) References Cited

U.S. PATENT DOCUMENTS

| | | | |
|---|---|---|---|
| 3,636,956 A | 1/1972 | Schneider | |
| 3,687,135 A | 8/1972 | Stroganov et al. | |
| 3,839,743 A | 10/1974 | Schwarcz | |
| 3,900,632 A | 8/1975 | Robinson | |
| 4,104,410 A | 8/1978 | Malecki | |
| 4,110,497 A | 8/1978 | Hoel | |
| 4,321,711 A | 3/1982 | Mano | |
| 4,346,028 A | 8/1982 | Griffith | |
| 4,547,416 A | 10/1985 | Reed et al. | |
| 4,596,574 A | 6/1986 | Urist | |
| 4,599,085 A | 7/1986 | Riess et al. | |
| 4,612,009 A | 9/1986 | Drobnik et al. | |
| 4,633,873 A | 1/1987 | Dumican et al. | |
| 4,656,083 A | 4/1987 | Hoffman et al. | |
| 4,698,196 A | 10/1987 | Fabian et al. | |
| 4,702,884 A | 10/1987 | Goldstein | |
| 4,718,907 A | 1/1988 | Karwoski et al. | |
| 4,722,335 A | 2/1988 | Vilasi | |
| 4,723,549 A | 2/1988 | Wholey et al. | |

(Continued)

FOREIGN PATENT DOCUMENTS

DE  44 07 079  9/1994

(Continued)

OTHER PUBLICATIONS

Answers.com blow molding; retrieved from www.answers.com/blow%20molding#Stretch_blow_molding, Jun. 26, 2009, 11 pgs.

(Continued)

*Primary Examiner*—Monica A Huson
(74) *Attorney, Agent, or Firm*—Squire, Sanders & Dempsey L.L.P.

(57) ABSTRACT

Methods of manufacturing a radially expandable stent, including radial expansion and axial elongation of a polymer tube, are disclosed.

5 Claims, 3 Drawing Sheets

U.S. PATENT DOCUMENTS

| | | | |
|---|---|---|---|
| 4,732,152 A | 3/1988 | Wallstén et al. |
| 4,733,665 A | 3/1988 | Palmaz |
| 4,739,762 A | 4/1988 | Palmaz |
| 4,740,207 A | 4/1988 | Kreamer |
| 4,743,252 A | 5/1988 | Martin, Jr. et al. |
| 4,768,507 A | 9/1988 | Fischell et al. |
| 4,776,337 A | 10/1988 | Palmaz |
| 4,800,882 A | 1/1989 | Gianturco |
| 4,816,339 A | 3/1989 | Tu et al. |
| 4,818,559 A | 4/1989 | Hama et al. |
| 4,850,999 A | 7/1989 | Planck |
| 4,877,030 A | 10/1989 | Beck et al. |
| 4,878,906 A | 11/1989 | Lindemann et al. |
| 4,879,135 A | 11/1989 | Greco et al. |
| 4,886,062 A | 12/1989 | Wiktor |
| 4,902,289 A | 2/1990 | Yannas |
| 4,957,687 A | 9/1990 | Akman et al. |
| 4,977,901 A | 12/1990 | Ofstead |
| 4,987,025 A | 1/1991 | Shiraki et al. |
| 4,994,298 A | 2/1991 | Yasuda |
| 5,019,090 A | 5/1991 | Pinchuk |
| 5,028,597 A | 7/1991 | Kodama et al. |
| 5,059,211 A | 10/1991 | Stack et al. |
| 5,062,829 A | 11/1991 | Pryor et al. |
| 5,084,065 A | 1/1992 | Weldon et al. |
| 5,085,629 A | 2/1992 | Goldberg et al. |
| 5,087,394 A | 2/1992 | Keith |
| 5,100,429 A | 3/1992 | Sinofsky et al. |
| 5,104,410 A | 4/1992 | Chowdhary |
| 5,108,416 A | 4/1992 | Ryan et al. |
| 5,108,417 A | 4/1992 | Sawyer |
| 5,108,755 A | 4/1992 | Daniels et al. |
| 5,112,457 A | 5/1992 | Marchant |
| 5,116,365 A | 5/1992 | Hillstead |
| 5,123,917 A | 6/1992 | Lee |
| 5,147,302 A | 9/1992 | Euteneuer et al. |
| 5,156,623 A | 10/1992 | Hakamatsuka et al. |
| 5,163,951 A | 11/1992 | Pinchuk et al. |
| 5,163,952 A | 11/1992 | Froix |
| 5,163,958 A | 11/1992 | Pinchuk |
| 5,167,614 A | 12/1992 | Tessmann et al. |
| 5,192,311 A | 3/1993 | King et al. |
| 5,197,977 A | 3/1993 | Hoffman, Jr. et al. |
| 5,234,456 A | 8/1993 | Silvestrini |
| 5,234,457 A | 8/1993 | Andersen |
| 5,236,447 A | 8/1993 | Kubo et al. |
| 5,279,594 A | 1/1994 | Jackson |
| 5,282,860 A | 2/1994 | Matsuno et al. |
| 5,289,831 A | 3/1994 | Bosley |
| 5,290,271 A | 3/1994 | Jernberg |
| 5,306,286 A | 4/1994 | Stack et al. |
| 5,306,294 A | 4/1994 | Winston et al. |
| 5,328,471 A | 7/1994 | Slepian |
| 5,330,500 A | 7/1994 | Song |
| 5,342,348 A | 8/1994 | Kaplan |
| 5,342,395 A | 8/1994 | Jarrett et al. |
| 5,342,621 A | 8/1994 | Eury |
| 5,356,433 A | 10/1994 | Rowland et al. |
| 5,383,925 A | 1/1995 | Schmitt |
| 5,385,580 A | 1/1995 | Schmitt |
| 5,389,106 A | 2/1995 | Tower |
| 5,399,666 A | 3/1995 | Ford |
| 5,423,885 A | 6/1995 | Williams |
| 5,441,515 A | 8/1995 | Khosravi et al. |
| 5,443,458 A | 8/1995 | Eury et al. |
| 5,443,500 A | 8/1995 | Sigwart |
| 5,455,040 A | 10/1995 | Marchant |
| 5,464,650 A | 11/1995 | Berg et al. |
| 5,500,013 A | 3/1996 | Buscemi et al. |
| 5,502,158 A | 3/1996 | Sinclair et al. |
| 5,514,379 A | 5/1996 | Weissleder et al. |
| 5,527,337 A | 6/1996 | Stack et al. |
| 5,545,408 A | 8/1996 | Trigg et al. |
| 5,554,120 A | 9/1996 | Chen et al. |
| 5,556,413 A | 9/1996 | Lam |
| 5,578,046 A | 11/1996 | Liu et al. |
| 5,578,073 A | 11/1996 | Haimovich et al. |
| 5,591,199 A | 1/1997 | Porter et al. |
| 5,591,607 A | 1/1997 | Gryaznov et al. |
| 5,593,403 A | 1/1997 | Buscemi |
| 5,593,434 A | 1/1997 | Williams |
| 5,599,301 A | 2/1997 | Jacobs et al. |
| 5,599,922 A | 2/1997 | Gryaznov et al. |
| 5,605,696 A | 2/1997 | Eury et al. |
| 5,607,442 A | 3/1997 | Fischell et al. |
| 5,607,467 A | 3/1997 | Froix |
| 5,618,299 A | 4/1997 | Khosravi et al. |
| 5,628,786 A | 5/1997 | Banas et al. |
| 5,629,077 A | 5/1997 | Turnlund et al. |
| 5,631,135 A | 5/1997 | Gryaznov et al. |
| 5,632,771 A | 5/1997 | Boatman et al. |
| 5,632,840 A | 5/1997 | Campbell |
| 5,637,113 A | 6/1997 | Tartaglia et al. |
| 5,649,977 A | 7/1997 | Campbell |
| 5,667,767 A | 9/1997 | Greff et al. |
| 5,667,796 A | 9/1997 | Otten |
| 5,670,161 A | 9/1997 | Healy et al. |
| 5,670,558 A | 9/1997 | Onishi et al. |
| 5,693,085 A | 12/1997 | Buirge et al. |
| 5,700,286 A | 12/1997 | Tartaglia et al. |
| 5,707,385 A | 1/1998 | Williams |
| 5,711,763 A | 1/1998 | Nonami et al. |
| 5,716,981 A | 2/1998 | Hunter et al. |
| 5,725,549 A | 3/1998 | Lam |
| 5,726,297 A | 3/1998 | Gryaznov et al. |
| 5,728,751 A | 3/1998 | Patnaik |
| 5,733,326 A | 3/1998 | Tomonto et al. |
| 5,733,330 A | 3/1998 | Cox |
| 5,733,564 A | 3/1998 | Lehtinen |
| 5,733,925 A | 3/1998 | Kunz et al. |
| 5,741,881 A | 4/1998 | Patnaik |
| 5,756,457 A | 5/1998 | Wang et al. |
| 5,756,476 A | 5/1998 | Epstein et al. |
| 5,765,682 A | 6/1998 | Bley et al. |
| 5,766,204 A | 6/1998 | Porter et al. |
| 5,766,239 A | 6/1998 | Cox |
| 5,766,710 A | 6/1998 | Turnlund et al. |
| 5,769,883 A | 6/1998 | Buscemi et al. |
| 5,780,807 A | 7/1998 | Saunders |
| 5,800,516 A | 9/1998 | Fine et al. |
| 5,811,447 A | 9/1998 | Kunz et al. |
| 5,824,049 A | 10/1998 | Ragheb et al. |
| 5,830,178 A | 11/1998 | Jones et al. |
| 5,830,461 A | 11/1998 | Billiar |
| 5,830,879 A | 11/1998 | Isner |
| 5,833,651 A | 11/1998 | Donovan et al. |
| 5,834,582 A | 11/1998 | Sinclair et al. |
| 5,836,962 A | 11/1998 | Gianotti |
| 5,837,313 A | 11/1998 | Ding et al. |
| 5,837,835 A | 11/1998 | Gryaznov et al. |
| 5,840,083 A | 11/1998 | Braach-Maksvytis |
| 5,851,508 A | 12/1998 | Greff et al. |
| 5,853,408 A | 12/1998 | Muni |
| 5,854,207 A | 12/1998 | Lee et al. |
| 5,855,612 A | 1/1999 | Ohthuki et al. |
| 5,855,618 A | 1/1999 | Patnaik et al. |
| 5,858,746 A | 1/1999 | Hubbell et al. |
| 5,865,814 A | 2/1999 | Tuch |
| 5,868,781 A | 2/1999 | Killion |
| 5,873,904 A | 2/1999 | Ragheb et al. |
| 5,874,101 A | 2/1999 | Zhong et al. |
| 5,874,109 A | 2/1999 | Ducheyne et al. |
| 5,874,165 A | 2/1999 | Drumheller |
| 5,876,743 A | 3/1999 | Ibsen et al. |

| Patent | Kind | Date | Inventor |
|---|---|---|---|
| 5,877,263 | A | 3/1999 | Patnaik et al. |
| 5,879,713 | A | 3/1999 | Roth et al. |
| 5,888,533 | A | 3/1999 | Dunn |
| 5,891,192 | A | 4/1999 | Murayama et al. |
| 5,891,386 | A * | 4/1999 | Deitermann et al. ........ 264/526 |
| 5,897,955 | A | 4/1999 | Drumheller |
| 5,906,759 | A | 5/1999 | Richter |
| 5,914,182 | A | 6/1999 | Drumheller |
| 5,916,870 | A | 6/1999 | Lee et al. |
| 5,922,005 | A | 7/1999 | Richter et al. |
| 5,942,209 | A | 8/1999 | Leavitt et al. |
| 5,948,428 | A | 9/1999 | Lee et al. |
| 5,954,744 | A | 9/1999 | Phan et al. |
| 5,957,975 | A | 9/1999 | Lafont et al. |
| 5,965,720 | A | 10/1999 | Gryaznov et al. |
| 5,971,954 | A | 10/1999 | Conway et al. |
| 5,976,182 | A | 11/1999 | Cox |
| 5,980,564 | A | 11/1999 | Stinson |
| 5,980,928 | A | 11/1999 | Terry |
| 5,980,972 | A | 11/1999 | Ding |
| 5,981,568 | A | 11/1999 | Kunz et al. |
| 5,986,169 | A | 11/1999 | Gjunter |
| 5,997,468 | A | 12/1999 | Wolff et al. |
| 6,010,445 | A | 1/2000 | Armini et al. |
| 6,015,541 | A | 1/2000 | Greff et al. |
| 6,042,875 | A | 3/2000 | Ding et al. |
| 6,048,964 | A | 4/2000 | Lee et al. |
| 6,051,648 | A | 4/2000 | Rhee et al. |
| 6,056,993 | A | 5/2000 | Leidner et al. |
| 6,060,451 | A | 5/2000 | DiMaio et al. |
| 6,066,156 | A | 5/2000 | Yan |
| 6,071,266 | A | 6/2000 | Kelley |
| 6,074,659 | A | 6/2000 | Kunz et al. |
| 6,080,177 | A | 6/2000 | Igaki et al. |
| 6,080,488 | A | 6/2000 | Hostettler et al. |
| 6,083,258 | A | 7/2000 | Yadav |
| 6,093,463 | A | 7/2000 | Thakrar |
| 6,096,070 | A | 8/2000 | Ragheb et al. |
| 6,096,525 | A | 8/2000 | Patnaik |
| 6,099,562 | A | 8/2000 | Ding et al. |
| 6,103,230 | A | 8/2000 | Billiar et al. |
| 6,107,416 | A | 8/2000 | Patnaik et al. |
| 6,110,188 | A | 8/2000 | Narciso, Jr. |
| 6,113,629 | A | 9/2000 | Ken |
| 6,117,979 | A | 9/2000 | Hendriks et al. |
| 6,120,536 | A | 9/2000 | Ding et al. |
| 6,120,904 | A | 9/2000 | Hostettler et al. |
| 6,121,027 | A | 9/2000 | Clapper et al. |
| 6,125,523 | A | 10/2000 | Brown et al. |
| 6,127,173 | A | 10/2000 | Eckstein et al. |
| 6,129,761 | A | 10/2000 | Hubbell |
| 6,129,928 | A | 10/2000 | Sarangapani et al. |
| 6,150,630 | A | 11/2000 | Perry et al. |
| 6,153,252 | A | 11/2000 | Hossainy et al. |
| 4,776,337 | A | 12/2000 | Palmaz |
| 6,159,951 | A | 12/2000 | Karpeisky et al. |
| 6,160,084 | A | 12/2000 | Langer et al. |
| 6,165,212 | A | 12/2000 | Dereume et al. |
| 6,166,130 | A | 12/2000 | Rhee et al. |
| 6,169,170 | B1 | 1/2001 | Gryaznov et al. |
| 6,171,609 | B1 | 1/2001 | Kunz |
| 6,174,330 | B1 | 1/2001 | Stinson |
| 6,177,523 | B1 | 1/2001 | Reich et al. |
| 6,183,505 | B1 | 2/2001 | Mohn, Jr. et al. |
| 6,187,045 | B1 | 2/2001 | Fehring et al. |
| 6,210,715 | B1 | 4/2001 | Starling et al. |
| 6,224,626 | B1 | 5/2001 | Steinke |
| 6,228,845 | B1 | 5/2001 | Donovan et al. |
| 6,240,616 | B1 | 6/2001 | Yan |
| 6,245,076 | B1 | 6/2001 | Yan |
| 6,245,103 | B1 | 6/2001 | Stinson |
| 6,248,344 | B1 | 6/2001 | Ylanen et al. |
| 6,251,135 | B1 | 6/2001 | Stinson et al. |
| 6,251,142 | B1 | 6/2001 | Bernacca et al. |
| 6,273,913 | B1 | 8/2001 | Wright et al. |
| 6,281,262 | B1 | 8/2001 | Shikinami |
| 6,284,333 | B1 | 9/2001 | Wang et al. |
| 6,287,332 | B1 | 9/2001 | Bolz et al. |
| 6,290,721 | B1 | 9/2001 | Heath |
| 6,293,966 | B1 | 9/2001 | Frantzen |
| 6,303,901 | B1 | 10/2001 | Perry et al. |
| 6,312,459 | B1 | 11/2001 | Huang et al. |
| 6,327,772 | B1 | 12/2001 | Zadno-Azizi et al. |
| 4,733,665 | C2 | 1/2002 | Palmaz |
| 6,360,577 | B2 * | 3/2002 | Austin .................. 72/402 |
| 6,375,826 | B1 | 4/2002 | Wang et al. |
| 6,379,381 | B1 | 4/2002 | Hossainy et al. |
| 6,387,121 | B1 | 5/2002 | Alt |
| 6,388,043 | B1 | 5/2002 | Langer et al. |
| 6,395,326 | B1 | 5/2002 | Castro et al. |
| 6,409,761 | B1 | 6/2002 | Jang |
| 6,423,092 | B2 | 7/2002 | Datta et al. |
| 6,461,632 | B1 | 10/2002 | Gogolewski |
| 6,464,720 | B2 | 10/2002 | Boatman et al. |
| 6,479,565 | B1 | 11/2002 | Stanley |
| 6,485,512 | B1 | 11/2002 | Cheng |
| 6,492,615 | B1 | 12/2002 | Flanagan |
| 6,494,908 | B1 | 12/2002 | Huxel et al. |
| 6,495,156 | B2 | 12/2002 | Wenz et al. |
| 6,500,146 | B1 * | 12/2002 | Pinchuk et al. .......... 604/96.01 |
| 6,511,748 | B1 | 1/2003 | Barrows |
| 6,517,888 | B1 | 2/2003 | Weber |
| 6,527,801 | B1 | 3/2003 | Dutta |
| 6,537,589 | B1 | 3/2003 | Chae et al. |
| 6,539,607 | B1 | 4/2003 | Fehring et al. |
| 6,540,777 | B2 | 4/2003 | Stenzel |
| 6,554,854 | B1 | 4/2003 | Flanagan |
| 6,565,599 | B1 | 5/2003 | Hong et al. |
| 6,569,191 | B1 | 5/2003 | Hogan |
| 6,569,193 | B1 | 5/2003 | Cox et al. |
| 6,572,672 | B2 | 6/2003 | Yadav et al. |
| 6,572,813 | B1 | 6/2003 | Zhang et al. |
| 6,574,851 | B1 | 6/2003 | Mirizzi |
| 6,585,755 | B2 | 7/2003 | Jackson et al. |
| 6,592,614 | B2 | 7/2003 | Lenker et al. |
| 6,592,617 | B2 | 7/2003 | Thompson |
| 6,613,072 | B2 | 9/2003 | Lau et al. |
| 6,626,939 | B1 | 9/2003 | Burnside et al. |
| 6,635,269 | B1 | 10/2003 | Jennissen |
| 6,645,243 | B2 | 11/2003 | Vallana et al. |
| 6,645,422 | B2 | 11/2003 | Jung et al. |
| 6,656,162 | B2 | 12/2003 | Santini, Jr. et al. |
| 6,664,335 | B2 | 12/2003 | Krishnan |
| 6,666,214 | B2 | 12/2003 | Canham |
| 6,667,049 | B2 | 12/2003 | Janas et al. |
| 6,669,723 | B2 | 12/2003 | Killion et al. |
| 6,676,697 | B1 | 1/2004 | Richter |
| 6,679,980 | B1 | 1/2004 | Andreacchi |
| 6,689,375 | B1 | 2/2004 | Wahlig et al. |
| 6,695,920 | B1 | 2/2004 | Pacetti et al. |
| 6,706,273 | B1 | 3/2004 | Roessler |
| 6,709,379 | B1 | 3/2004 | Brandau et al. |
| 6,719,934 | B2 | 4/2004 | Stinson |
| 6,719,989 | B1 | 4/2004 | Matsushima et al. |
| 6,720,402 | B2 | 4/2004 | Langer et al. |
| 6,746,773 | B2 | 6/2004 | Llanos et al. |
| 6,752,826 | B2 | 6/2004 | Holloway et al. |
| 6,753,007 | B2 | 6/2004 | Haggard et al. |
| 6,764,505 | B1 | 7/2004 | Hossainy et al. |
| 6,818,063 | B1 | 11/2004 | Kerrigan |
| 6,846,323 | B2 | 1/2005 | Yip et al. |
| 7,066,952 | B2 | 6/2006 | Igaki |
| 7,070,615 | B1 | 7/2006 | Igaki |
| 7,083,639 | B2 * | 8/2006 | Guinan et al. ............ 623/1.1 |
| 7,128,868 | B2 | 10/2006 | Eidenschink |
| 2001/0014821 | A1 * | 8/2001 | Juman .................. 623/1.11 |

| | | |
|---|---|---|
| 2001/0044652 A1 | 11/2001 | Moore |
| 2002/0002399 A1 | 1/2002 | Huxel et al. |
| 2002/0004060 A1 | 1/2002 | Heublein et al. |
| 2002/0004101 A1 | 1/2002 | Ding et al. |
| 2002/0041059 A1* | 4/2002 | Jung et al. .................. 264/529 |
| 2002/0062148 A1 | 5/2002 | Hart |
| 2002/0065553 A1 | 5/2002 | Weber |
| 2002/0077592 A1 | 6/2002 | Barry |
| 2002/0111590 A1 | 8/2002 | Davila et al. |
| 2002/0116050 A1 | 8/2002 | Kocur |
| 2002/0125617 A1 | 9/2002 | Skinner et al. |
| 2002/0138133 A1 | 9/2002 | Lenz et al. |
| 2002/0151965 A1 | 10/2002 | Roth |
| 2002/0161114 A1 | 10/2002 | Gunatillake et al. |
| 2003/0028241 A1 | 2/2003 | Stinson |
| 2003/0028246 A1 | 2/2003 | Palmaz et al. |
| 2003/0033001 A1 | 2/2003 | Igaki |
| 2003/0055488 A1 | 3/2003 | Igaki |
| 2003/0083732 A1* | 5/2003 | Stinson ...................... 623/1.15 |
| 2003/0093107 A1 | 5/2003 | Parsonage et al. |
| 2003/0100865 A1 | 5/2003 | Santini, Jr. et al. |
| 2003/0105518 A1 | 6/2003 | Dutta |
| 2003/0105530 A1 | 6/2003 | Pirhonen et al. |
| 2003/0171053 A1 | 9/2003 | Sanders |
| 2003/0187158 A1 | 10/2003 | Preuschen et al. |
| 2003/0187495 A1 | 10/2003 | Cully et al. |
| 2003/0208254 A1 | 11/2003 | Shortt |
| 2003/0208259 A1 | 11/2003 | Penhasi |
| 2003/0209835 A1 | 11/2003 | Chun et al. |
| 2003/0226833 A1 | 12/2003 | Shapovalov et al. |
| 2003/0236563 A1 | 12/2003 | Fifer |
| 2004/0000361 A1 | 1/2004 | Trozera |
| 2004/0093077 A1 | 5/2004 | White et al. |
| 2004/0098090 A1 | 5/2004 | Williams et al. |
| 2004/0098095 A1 | 5/2004 | Burnside et al. |
| 2004/0111149 A1 | 6/2004 | Stinson |
| 2004/0127970 A1 | 7/2004 | Saunders et al. |
| 2004/0143317 A1 | 7/2004 | Stinson et al. |
| 2004/0167610 A1 | 8/2004 | Fleming, III |
| 2004/0181271 A1 | 9/2004 | DeSimone et al. |
| 2005/0004663 A1 | 1/2005 | Llanos et al. |
| 2005/0137678 A1 | 6/2005 | Varma |
| 2005/0177130 A1 | 8/2005 | Konstantino et al. |
| 2005/0187615 A1 | 8/2005 | Williams et al. |
| 2005/0196485 A1 | 9/2005 | Cass et al. |
| 2006/0020330 A1 | 1/2006 | Huang et al. |
| 2006/0211952 A1 | 9/2006 | Kennedy |
| 2006/0224226 A1 | 10/2006 | Huang et al. |
| 2007/0253996 A1 | 11/2007 | Bin et al. |
| 2007/0253999 A1 | 11/2007 | Huang et al. |
| 2007/0282433 A1 | 12/2007 | Limon et al. |
| 2007/0290412 A1 | 12/2007 | Capek et al. |
| 2007/0293938 A1 | 12/2007 | Gale et al. |
| 2008/0001333 A1 | 1/2008 | Kleine et al. |
| 2009/0001633 A1 | 1/2009 | Limon et al. |
| 2009/0005860 A1 | 1/2009 | Huang et al. |
| 2009/0012598 A1 | 1/2009 | Abbate et al. |
| 2009/0146348 A1 | 6/2009 | Huang et al. |

FOREIGN PATENT DOCUMENTS

| | | |
|---|---|---|
| DE | 197 31 021 | 1/1999 |
| DE | 198 56 983 | 12/1999 |
| EP | 0 108 171 | 5/1984 |
| EP | 0 144 534 | 6/1985 |
| EP | 0 364 787 | 4/1990 |
| EP | 0 397 500 | 11/1990 |
| EP | 0 464 755 | 1/1992 |
| EP | 0 493 788 | 7/1992 |
| EP | 0 554 082 | 8/1993 |
| EP | 0 578 998 | 1/1994 |
| EP | 0 583 170 | 2/1994 |
| EP | 0 604 022 | 6/1994 |
| EP | 0 621 017 | 10/1994 |
| EP | 0 623 354 | 11/1994 |
| EP | 0 665 023 | 8/1995 |
| EP | 0 709 068 | 5/1996 |
| EP | 0 970 711 | 1/2000 |
| EP | 1 800 628 | 6/2007 |
| GB | 2 102 827 | 2/1983 |
| GB | 2 247 696 | 3/1992 |
| WO | WO 89/03232 | 4/1989 |
| WO | WO 90/01969 | 3/1990 |
| WO | WO 90/04982 | 5/1990 |
| WO | WO 90/06094 | 6/1990 |
| WO | WO 91/17744 | 11/1991 |
| WO | WO 91/17789 | 11/1991 |
| WO | WO 92/10218 | 6/1992 |
| WO | WO 93/06792 | 4/1993 |
| WO | WO 94/21196 | 9/1994 |
| WO | WO 95/29647 | 11/1995 |
| WO | WO 97/32546 | 9/1997 |
| WO | WO 98/04415 | 2/1998 |
| WO | WO 99/03515 | 1/1999 |
| WO | WO 99/16386 | 4/1999 |
| WO | WO 99/42147 | 8/1999 |
| WO | WO 00/12147 | 3/2000 |
| WO | WO 00/64506 | 11/2000 |
| WO | WO 01/01890 | 1/2001 |
| WO | WO 01/15633 | 3/2001 |
| WO | WO 03/034940 | 5/2003 |
| WO | WO 2004/023985 | 3/2004 |
| WO | WO 2004/067262 | 8/2004 |
| WO | WO 2006/014747 | 2/2006 |

OTHER PUBLICATIONS www.engineeringtoolbox.com/thermal/conductivity/d_429.html., Jun. 26, 2009, 4 pgs.

U.S. Appl. No. 10/317,435, filed Dec. 11, 2002, Hossainy et al.

Anonymous, *Bioabsorbable stent mounted on a catheter having optical coherence tomography capabilities*, Research Disclosure, Sep. 2004, pp. 1159-1162.

Ansari, *Tubal Reanastomosis Using Absorbable Stent*, International Journal of Fertility, vol. 23, No. 4, pp. 242-243 (1978).

Ansari, *End-to-end tubal anastomosis using an absorbable stent*, Fertility and Sterility, vol. 32(2), pp. 197-201 (Aug. 1979).

Bull, *Parylene Coating for Medical Applications*, Medical Product Manufacturing News 1 pg. (Mar. 1993).

Casper et al., *Fiber-Reinforced Absorbable Composite for Orthopedic Surgery*, Polymeric Materials Science and Engineering, 53: pp. 497-501 (1985).

Detweiler et al., *Sutureless Anastomosis of the Small Intestine and the Colon in Pigs Using an Absorbable Intraluminal Stent and Fibrin Glue*, Journal of Investigative Surgery, vol. 8(2), pp. 129-140 (Mar. 1995).

Detweiler et al., *Sutureless Cholecystojejunostomy in Pigs Using an Absorbable Intraluminal Stent and Fibrin Glue*, Journal of Investigative Surgery, vol. 9(1), pp. 13-26 (Jan./Feb. 1996).

Detweiler et al., *Sliding, Absorbable, Reinforced Ring and an Axially Driven Stent Placement Device for Sutureless Fibrin Glue Gastrointestinal Anastomisis*, Journal. Of Investigative Surgery, vol. 9(6), pp. 495-504 (Nov./Dec. 1996).

Detweiler et al., *Gastrointestinal Sutureless Anastomosis Using Fibrin Glue: Reinforcement of the Sliding Absorbable Intraluminal Nontoxic Stent and Development of a Stent Placement Device*, Journal of Investigative Surgery, vol. 9(2), pp. 111-130 (Mar./Apr. 1996).

Devanathan et al., *Polymeric Conformal Coatings for Implantable Electronic Devices*, IEEE Transactions on Biomedical Engineering, vol. BME-27(11), pp. 671-675 (1980).

Elbert et al., *Conjugate Addition Reactions Combined with Free-Radical Cross-Linking for the Design of Materials for Tissue Engineering*, Biomacromolecules 2, pp. 430-441 (2001).

Feng-Chun et al., *Assessment of Tissue Blood Flow Following Small Artery Welding with an Intraluminal Dissolvable Stent*, Microsurgery, vol. 19(3), pp. 148-152 (1999).

Hahn et al., *Glow Discharge Polymers as Coatings for Implanted Devices*, ISA, pp. 109-111 (1981).

Hahn et al., *Biocompatibility of Glow-Discharge-Polymerized Films and Vacuum-Deposited Parylene*, J Applied Polymer Sci, 38, pp. 55-64 (1984).

Kelley et al., *Totally Resorbable High-Strength Composite Material*, Advances in Biomedical Polymers, 35, pp. 75-85 (1987).

Kubies et al., *Microdomain Structure in polylactide-block-poly(ethylene oxide) copolymer films*, Biomaterials 21, pp. 529-536 (2000).

Kutryk et al., *Coronary Stenting: Current Perspectives*, a companion to the Handbook of Coronary Stents 16 pgs. (1999).

Mauduit et al., *Hydrolytic degradation of films prepared from blends of high and low molecular weight poly(DL-lactic acid)s*, J. Biomed. Mater. Res. v. 30, pp. 201-207 (1996).

Martin et al., *Enhancing the biological activity of immobilized osteopontin using a type-1 collagen affinity coating*, J. Biomed. Mater Res 70A, pp. 10-19 (2004).

Middleton et al., *Synthetic biodegradable polymers as orthopedic devices*, Biomaterials, vol. 21, pp. 2335-2346 (2000).

Muller et al., *Advances in Coronary Angioplasty: Endovascular Stents*, Coron. Arter. Dis., 1(4), pp. 438-448 (Jul./Aug. 1990).

Nichols et al., *Electrical Insulation of Implantable Devices by Composite Polymer Coatings*, ISA Transactions, 26(4), pp. 15-18 (1987).

Peuster et al., *A novel approach to temporary stenting: degradable cardiovascular stents produced from corrodible metal-results 6-18 months after implantation into New Zealand white rabbits*, Heart 86, pp. 563-569 (2001).

Pietrzak et al., *Bioresorbable implants—practical considerations*, Bone v. 19, No. 1, Supplement Jul. 1996: 109S-119S.

Pietrzak et al., *Bioabsorbable Fixation Devices: Status for the Craniomaxillofacial Surgeon*, J. Craniofaxial Surg. 2, pp. 92-96 (1997).

von Recum et al., *Degradation of polydispersed poly(L-lactic acid) to modulate lactic acid release*, Biomaterials 16, pp. 441-445 (1995).

Redman, *Clinical Experience with Vasovasostomy Utilizing Absorbable Intravasal Stent*, Urology, vol. 20(1), pp. 59-61 (Jul. 1982).

Rust et al., *The Effect of Absorbable Stenting on Postoperative Stenosis of the Surgically Enlarged Maxillary Sinus Ostia in a Rabbit Animal Model*, Archives of Otolaryngology, vol. 122(12) pp. 1395-1397 (Dec. 1996).

Schatz, *A View of Vascular Stents*, Circulation, 79(2), pp. 445-457 (Feb. 1989).

Schmidt et al., *Long-Term Implants of Parylene-C Coated Microelectrodes*, Med & Biol Eng & Comp, 26(1), pp. 96-101 (Jan. 1988).

Spagnuolo et al., *Gas 1 is induced by VE-cadherin and vascular endothelial growth factor and inhibits endothelial cell apoptosis*, Blood 103, pp. 3005-3012 (2004).

Tamai et al., *Initial and 6-Month Results of Biodegradable Poly-l-Lactic Acid Coronary Stents in Humans*, Circulation , pp. 399-404 (2000).

Tsui et al., *Biodegradable Polymeric Stents*, Current Interventional Cardiology Reports 3, pp. 10-17 (2001).

Völkel et al., *Targeting of immunoliposomes to endothelial cells using a single—chain Fv fragment directed against human endoglin (CD105)*, Biochemica et Biophysica Acta 1663, pp. 158-166 (2004).

Yau et al. Modern Size-Exclusion Liquid Chromatography, Wiley-Interscience Publication, (1979).

U.S. Appl. No. 10/956,911, filed Sep. 30, 2004, Durcan.

Search Report for PCT/US2006/026455 filed Jul. 3, 2006, mailed Oct. 19, 2006 11 pgs.

\* cited by examiner

METHOD OF FABRICATING A BIAXIALLY ORIENTED IMPLANTABLE MEDICAL DEVICE

CROSS-REFERENCE

This is a continuation-in-part of application Ser. No. 10/956,910 filed on Sep. 30, 2004.

BACKGROUND OF THE INVENTION

1. Field of the Invention

This invention relates to methods of forming radially expandable implantable medical devices with biaxial orientation.

2. Description of the State of the Art

This invention relates to radially expandable endoprostheses, which are adapted to be implanted in a bodily lumen. An "endoprosthesis" corresponds to an artificial device that is placed inside the body. A "lumen" refers to a cavity of a tubular organ such as a blood vessel.

A stent is an example of such an endoprosthesis. Stents are generally cylindrically shaped devices, which function to hold open and sometimes expand a segment of a blood vessel or other anatomical lumen such as urinary tracts and bile ducts. Stents are often used in the treatment of atherosclerotic stenosis in blood vessels. "Stenosis" refers to a narrowing or constriction of the diameter of a bodily passage or orifice. In such treatments, stents reinforce body vessels and prevent restenosis following angioplasty in the vascular system. "Restenosis" refers to the reoccurrence of stenosis in a blood vessel or heart valve after it has been treated (as by balloon angioplasty, stenting, or valvuloplasty) with apparent success.

The treatment of a diseased site or lesion with a stent involves both delivery and deployment of the stent. "Delivery" refers to introducing and transporting the stent through a bodily lumen to a region, such as a lesion, in a vessel that requires treatment. "Deployment" corresponds to the expanding of the stent within the lumen at the treatment region. Delivery and deployment of a stent are accomplished by positioning the stent about one end of a catheter, inserting the end of the catheter through the skin into a bodily lumen, advancing the catheter in the bodily lumen to a desired treatment location, expanding the stent at the treatment location, and removing the catheter from the lumen.

In the case of a balloon expandable stent, the stent is mounted about a balloon disposed on the catheter. Mounting the stent typically involves compressing or crimping the stent onto the balloon. The stent is then expanded by inflating the balloon. The balloon may then be deflated and the catheter withdrawn. In the case of a self-expanding stent, the stent may be secured to the catheter via a retractable sheath or a sock. When the stent is in a desired bodily location, the sheath may be withdrawn which allows the stent to self-expand.

The stent must be able to satisfy a number of mechanical requirements. First, the stent must be capable of withstanding the structural loads, namely radial compressive forces, imposed on the stent as it supports the walls of a vessel. Therefore, a stent must possess adequate radial strength. Radial strength, which is the ability of a stent to resist radial compressive forces, is due to strength and rigidity around a circumferential direction of the stent. Radial strength and rigidity, therefore, may also be described as, hoop or circumferential strength and rigidity.

Once expanded, the stent must adequately maintain its size and shape throughout its service life despite the various forces that may come to bear on it, including the cyclic loading induced by the beating heart. For example, a radially directed force may tend to cause a stent to recoil inward. Generally, it is desirable to minimize recoil.

In addition, the stent must possess sufficient flexibility to allow for crimping, expansion, and cyclic loading. Longitudinal flexibility is important to allow the stent to be maneuvered through a tortuous vascular path and to enable it to conform to a deployment site that may not be linear or may be subject to flexure. Finally, the stent must be biocompatible so as not to trigger any adverse vascular responses.

The structure of a stent is typically composed of scaffolding that includes a pattern or network of interconnecting structural elements often referred to in the art as struts or bar arms. The scaffolding can be formed from wires, tubes, or sheets of material rolled into a cylindrical shape. The scaffolding is designed so that the stent can be radially compressed (to allow crimping) and radially expanded (to allow deployment). A conventional stent is allowed to expand and contract through movement of individual structural elements of a pattern with respect to each other.

Additionally, a medicated stent may be fabricated by coating the surface of either a metallic or polymeric scaffolding with a polymeric carrier that includes an active or bioactive agent or drug. Polymeric scaffolding may also serve as a carrier of an active agent or drug.

Furthermore, it may be desirable for a stent to be biodegradable. In many treatment applications, the presence of a stent in a body may be necessary for a limited period of time until its intended function of, for example, maintaining vascular patency and/or drug delivery is accomplished. Therefore, stents fabricated from biodegradable, bioabsorbable, and/or bioerodable materials such as bioabsorbable polymers should be configured to completely erode only after the clinical need for them has ended.

In general, there are several important aspects in the mechanical behavior of polymers that affect stent design. Polymers tend to have lower strength than metals on a per unit mass basis. Therefore, polymeric stents typically have less circumferential strength and radial rigidity than metallic stents of the same or similar dimensions. Inadequate radial strength potentially contributes to a relatively high incidence of recoil of polymeric stents after implantation into vessels.

Another potential problem with polymeric stents is that their struts or bar arms can crack during crimping and expansion, especially for brittle polymers. The localized portions of the stent pattern subjected to substantial deformation tend to be the most vulnerable to failure. Furthermore, in order to have adequate mechanical strength, polymeric stents may require significantly thicker struts than a metallic stent, which results in an undesirably larger profile.

Conventional methods of constructing a stent from a polymer material involve extrusion of a polymer tube based on a single polymer or polymer blend and then laser cutting a pattern into the tube.

Therefore, it would be desirable to have methods of making biodegradable polymeric stents that are both strong and flexible.

SUMMARY OF THE INVENTION

Certain embodiments of the present invention are directed to a method for fabricating an implantable medical device such as a stent. The method may include radially deforming a polymeric tube about a cylindrical axis of the tube and axially deforming the tube along the cylindrical axis. The method may further include fabricating a stent from the radially and axially deformed tube.

DETAILED DESCRIPTION OF THE INVENTION

For the purposes of the present invention, the following terms and definitions apply:

The "glass transition temperature," $T_g$, is the temperature at which the amorphous domains of a polymer change from a brittle vitreous state to a solid deformable or ductile state at atmospheric pressure. In other words, the $T_g$ corresponds to the temperature where the onset of segmental motion in the chains of the polymer occurs. When an amorphous or semicrystalline polymer is exposed to an increasing temperature, the coefficient of expansion and the heat capacity of the polymer both increase as the temperature is raised, indicating increased molecular motion. As the temperature is raised the actual molecular volume in the sample remains constant, and so a higher coefficient of expansion points to an increase in free volume associated with the system and therefore increased freedom for the molecules to move. The increasing heat capacity corresponds to an increase in heat dissipation through movement. $T_g$ of a given polymer can be dependent on the heating rate and can be influenced by the thermal history of the polymer. Furthermore, the chemical structure of the polymer heavily influences the glass transition by affecting mobility.

"Stress" refers to force per unit area, as in the force acting through a small area within a plane. Stress can be divided into components, normal and parallel to the plane, called normal stress and shear stress, respectively. Tensile stress, for example, is a normal component of stress applied that leads to expansion (increase in length). In addition, compressive stress is a normal component of stress applied to materials resulting in their compaction (decrease in length). Stress may result in deformation of a material, which refers to a change in length. "Expansion" or "compression" may be defined as the increase or decrease in length of a sample of material when the sample is subjected to stress. "Strain" refers to the amount of expansion or compression that occurs in a material at a given stress or load. Strain may be expressed as a fraction or percentage of the original length, i.e., the change in length divided by the original length. Strain, therefore, is positive for expansion and negative for compression.

Furthermore, a property of a material that quantifies a degree of deformation with applied stress is the modulus. "Modulus" may be defined as the ratio of a component of stress or force per unit area applied to a material divided by the strain along an axis of applied force that results from the applied force. For example, a material has both a tensile and a compressive modulus.

The tensile stress on a material may be increased until it reaches a "tensile strength" which refers to the maximum tensile stress which a material will withstand prior to fracture. The ultimate tensile strength is calculated from the maximum load applied during a test divided by the original cross-sectional area. Similarly, "compressive strength" is the capacity of a material to withstand axially directed pushing forces. When the limit of compressive strength is reached, a material is crushed.

The term "elastic deformation" refers to deformation of an object in which the applied stress is small enough so that the object moves towards its original dimensions or essentially its original dimensions once the stress is released. However, an elastically deformed polymer material may be inhibited or prevented from returning to an undeformed state when the material is elastically deformed at a temperature above the $T_g$ and then quenched to a temperature below the $T_g$ of the polymer while in the deformed state. Below $T_g$, energy barriers may inhibit or prevent molecular movement that allows deformation or bulk relaxation. "Elastic limit" refers to the maximum stress that a material will withstand without permanent deformation. The term "plastic deformation" refers to permanent deformation that occurs in a material under stress after elastic limits have been exceeded.

"Neutral axis" refers to a line or plane in a structural member subjected to a stress at which the strain is zero. For example, a beam in flexure due to stress (e.g., at a top face) has tension on one side (e.g., the bottom face) and compression on the other (e.g., the top face). The neutral axis lies between the two sides at a location or locations of zero strain. The neutral axis may correspond to a surface. For a linear, symmetric, homogeneous beam, the neutral axis is at the geometric centroid (center of mass) of the beam. However, the neutral axis for a curved beam does not coincide with the centroidal axis.

The strain increases in either direction away from the neutral axis. The length and strain of material elements parallel to the centroidal axis depend on both the distance of a material element from that axis and the radius of curvature of the curved beam.

The term "implantable medical device" is intended to include, but is not limited to, self-expandable stents, balloon-expandable stents, stent-grafts, and grafts (e.g., aortic grafts). The implantable medical devices that relate to the embodiments described herein typically include an underlying scaffolding or substrate. The underlying structure or substrate of the device can be of virtually any design. The substrate may have a polymer-based coating that may contain, for example, an active agent or drug for local administration at a diseased site. The active agent can be any substance capable of exerting a therapeutic or prophylactic effect.

Polymers can be biostable, bioabsorbable, biodegradable or bioerodable. Biostable refers to polymers that are not biodegradable. The terms biodegradable, bioabsorbable, and bioerodable are used interchangeably and refer to polymers that are capable of being completely degraded and/or eroded when exposed to bodily fluids such as blood and can be gradually resorbed, absorbed, and/or eliminated by the body. The processes of breaking down and eventual absorption and elimination of the polymer can be caused by, for example, hydrolysis, metabolic processes, bulk or surface erosion, and the like.

It is understood that after the process of degradation, erosion, absorption, and/or resorption has been completed, no part of the stent will remain or in the case of coating applications on a biostable scaffolding, no polymer will remain on the device. In some embodiments, very negligible traces or residue may be left behind. For stents made from a biodegradable polymer, the stent is intended to remain in the body for a duration of time until its intended function of, for example, maintaining vascular patency and/or drug delivery is accomplished.

The underlying structure or substrate of an implantable medical device, such as a stent can be completely or at least in part be made from a biodegradable polymer or combination of biodegradable polymers, a biostable polymer or combination of biostable polymers, or a combination of biodegradable and biostable polymers. Additionally, a polymer-based coating for a surface of a device can be a biodegradable polymer or combination of biodegradable polymers, a biostable polymer or combination of biostable polymers, or a combination of biodegradable and biostable polymers.

Representative examples of polymers that may be used to fabricate or coat an implantable medical device include, but are not limited to, poly(N-acetylglucosamine) (Chitin), Chitosan, poly(hydroxyvalerate), poly(lactide-co-glycolide), poly(hydroxybutyrate), poly(hydroxybutyrate-co-valerate), polyorthoester, polyanhydride, poly(glycolic acid), poly(glycolide), poly(L-lactic acid), poly(L-lactide), poly(D,L-lactic acid), poly(D,L-lactide), poly(caprolactone), poly(trimethylene carbonate), polyester amide, poly(glycolic acid-co-trimethylene carbonate), co-poly(ether-esters) (e.g. PEO/PLA), polyphosphazenes, biomolecules (such as fibrin, fibrinogen, cellulose, starch, collagen and hyaluronic acid), polyurethanes, silicones, polyesters, polyolefins, polyisobutylene and ethylene-alphaolefin copolymers, acrylic polymers and copolymers other than polyacrylates, vinyl halide polymers and copolymers (such as polyvinyl chloride), polyvinyl ethers (such as polyvinyl methyl ether), polyvinylidene halides (such as polyvinylidene chloride), polyacrylonitrile, polyvinyl ketones, polyvinyl aromatics (such as polystyrene), polyvinyl esters (such as polyvinyl acetate), acrylonitrile-styrene copolymers, ABS resins, polyamides (such as Nylon 66 and polycaprolactam), polycarbonates, polyoxymethylenes, polyimides, polyethers, polyurethanes, rayon, rayon-triacetate, cellulose, cellulose acetate, cellulose butyrate, cellulose acetate butyrate, cellophane, cellulose nitrate, cellulose propionate, cellulose ethers, and carboxymethyl cellulose. Another type of polymer based on poly(lactic acid) that can be used includes graft copolymers, and block copolymers, such as AB block-copolymers ("diblock-copolymers") or ABA block-copolymers ("triblock-copolymers"), or mixtures thereof.

Additional representative examples of polymers that may be especially well suited for use in fabricating or coating an implantable medical device include ethylene vinyl alcohol copolymer (commonly known by the generic name EVOH or by the trade name EVAL), poly(butyl methacrylate), poly(vinylidene fluoride-co-hexafluororpropene) (e.g., SOLEF 21508, available from Solvay Solexis PVDF, Thorofare, N.J.), polyvinylidene fluoride (otherwise known as KYNAR, available from ATOFINA Chemicals, Philadelphia, Pa.), ethylene-vinyl acetate copolymers, and polyethylene glycol.

Implantable medical devices are typically subjected to stress during use, both before and during treatment. "Use" includes, but is not limited to, manufacturing, assembling (e.g., crimping stent on a catheter), delivery of stent into and through a bodily lumen to a treatment site, and deployment of stent at a treatment site. Both a scaffolding and a coating on a scaffolding experience stress that result in strain in the scaffolding and/or coating. For example, during deployment, the scaffolding of a stent can be exposed to stress caused by the radial expansion of the stent body. In addition, the scaffolding and/or coating may be exposed to stress when it is mounted on a catheter from crimping or compression of the stent.

It is well known by those skilled in the art that molecular orientation or alignment of polymer chains in a polymer is a particularly important phenomenon that strongly influences bulk polymer properties. For example, strength, modulus, yield stress behavior, and elongation to break are a few of the important properties that may be influenced by orientation of polymer chains in a polymer. Molecular orientation refers to the relative orientation of polymer chains along a longitudinal or covalent axis of the polymer chains. A polymer with a high degree of molecular orientation has polymer chains that are aligned or close to being aligned along their covalent axes. Polymer chain alignment in a polymeric material may be induced by applying stress along a preferred direction.

Polymers in the solid state may have amorphous regions and crystalline regions. Crystalline regions include highly oriented polymer chains in an ordered structure. An oriented crystalline structure tends to have high strength and high modulus (low elongation with applied stress) along an axis of alignment of polymer chains.

On the other hand, amorphous polymer regions include relatively disordered polymer chains that may or may not be oriented in a particular direction. However, a high degree of molecular orientation may be induced even in an amorphous region. An oriented amorphous region also tends to have high strength and high modulus along an axis of alignment of polymer chains. Additionally, for some polymers under some conditions, induced alignment in an amorphous polymer may be accompanied by crystallization of the amorphous polymer into an ordered structure.

A polymer may be completely amorphous, partially crystalline, or almost completely crystalline. A partially crystalline polymer includes crystalline regions separated by amorphous regions. The crystalline regions do not necessarily have the same or similar orientation of polymer chains. However, a high degree of orientation of crystallites may be induced by applying stress to a semi-crystalline polymer. The stress may also induce orientation in the amorphous regions.

The degree of polymer chain alignment induced with applied stress may depend upon the temperature of the polymer. For example, below the $T_g$ of a polymer, polymer segments may not have sufficient energy to move past one another. In general, polymer chain alignment may not be induced without sufficient segmental mobility. Above $T_g$, polymer chain alignment may be readily induced with applied stress since rotation of polymer chains, and hence segmental mobility, is possible. Between $T_g$ and the melting temperature of the polymer, $T_m$, rotational barriers exist. However, the barriers are not great enough to substantially prevent segmental mobility. As the temperature of a polymer is increased above $T_g$, the energy barriers to rotation decrease and segmental mobility of polymer chains tends to increase. Thus, as the temperature increases, polymer chain alignment is more easily induced with applied stress.

Consequently, the amount of deformation depends on the temperature of a polymeric material. Therefore, it may be necessary for the increase in temperature of a polymer material to be uniform or relatively uniform to achieve uniform or relatively uniform deformation throughout a volume of a polymer material. In the radial deformation of a tube, for example, a more uniform deformation may result in a more uniform induced circumferential polymer alignment and induced mechanical properties. In general, the more uniform the enhancement of material properties due to deformation, the more mechanically stable the device is. In particular, localized regions with unfavorable mechanical properties that are susceptible to mechanical failure may be reduced or eliminated by more uniform heating, or by a more uniform increase in the temperature of the polymeric material.

Rearrangement of polymer chains may take place when a polymer is stressed in an elastic region and in a plastic region of the polymer material. A polymer stressed beyond its elastic limit to a plastic region generally retains its stressed configuration and corresponding induced polymer chain alignment when stress is removed. The polymer chains may become oriented in the direction of the applied stress. The stressed polymer material may have a higher tensile strength and modulus in the direction of the applied stress.

Additionally, heating a polymer may facilitate deformation of a polymer under stress, and hence, modification of the mechanical properties of the polymer. A polymer deformed elastically with stress facilitated with heating may retain induced polymer chain alignment by cooling the polymer before the polymer chains in the polymer relax to or towards an unstrained state.

Since highly oriented regions in polymers tend to have a high strength and modulus, it may be desirable to incorporate processes that induce alignment of polymer chains along one or more preferred axes or directions into manufacturing methods of implantable medical devices. Various embodiments of methods for fabricating implantable medical devices are described herein. In some embodiments, an implantable medical device may be fabricated from a polymer conduit or tube. The tube may be cylindrical or substantially cylindrical in shape.

Figure 1:
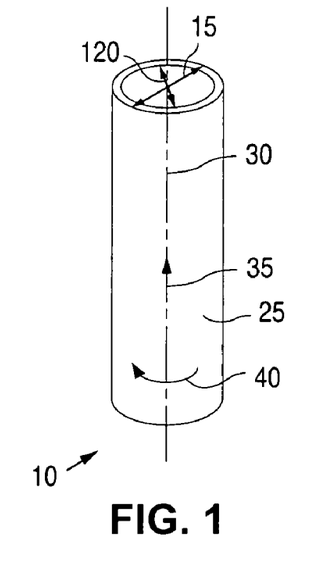
FIG. 1 depicts a tube.

For example, FIG. 1 depicts a tube 10. Tube 10 is a cylinder with an outside diameter 15 and an inside diameter 20. FIG. 1 also depicts a surface 25 and a cylindrical axis 30 of tube 10. In some embodiments, the diameter of the polymer tube prior to fabrication of an implantable medical device may be between about 0.2 mm and about 5.0 mm, or more narrowly between about 1 mm and about 3 mm.

Additionally, fabrication of an implantable medical device, such as a stent, may include forming a pattern that includes a plurality of interconnecting structural elements or struts on a tube. In some embodiments, forming a pattern on a tube may include laser cutting a pattern on the tube. Representative examples of lasers that may be used include, but are not limited to, excimer, carbon dioxide, and YAG. In other embodiments, chemical etching may be used to form a pattern on a tube.

It may be desirable to use a laser cutting technique which minimizes a size of a heat affected zone. A heat affected zone refers to a region of a target material affected by the heat of the laser. Heat from the laser may tend to melt at least a portion of polymer in the heat affected zone. The molecular orientation induced by applied stress may then be dissipated in the melted portion. The corresponding favorable change in mechanical properties may also be reduced.

Figure 2:
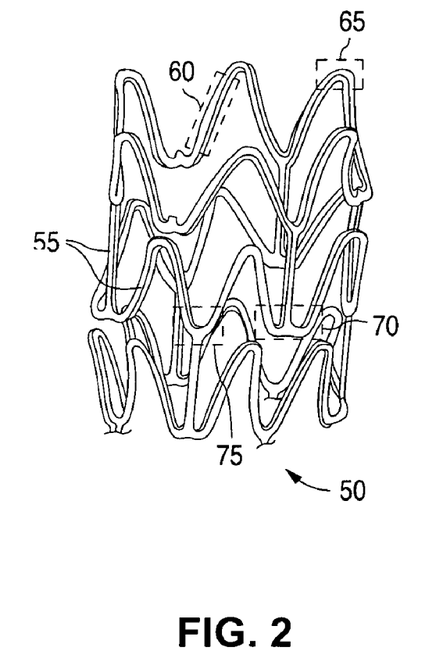
FIG. 2 depicts a stent.

FIG. 2 depicts an example of a three-dimensional view of a stent 50. Stent 50 includes a pattern with a number of interconnecting structural elements or struts 55. The embodiments disclosed herein are not limited to stents or to the stent pattern illustrated in FIG. 2. The embodiments are easily applicable to other patterns and other devices. The variations in the structure of patterns are virtually unlimited.

In general, a stent pattern is designed so that the stent can be radially compressed (crimped) and radially expanded (to allow deployment). The stresses involved during compression and expansion are generally distributed throughout various structural elements of the stent pattern. As a stent expands, various portions of the stent can deform to accomplish a radial expansion.

As shown in FIG. 2, the geometry or shape of stent 50 varies throughout its structure to allow radial expansion and compression. A pattern may include portions of struts that are straight or relatively straight, an example being a portion 60. In addition, patterns may include struts that include curved or bent portions as in sections 65, 70, and 75.

The pattern that makes up the stent allows the stent to be radially compressible and expandable and longitudinally flexible. Portions such as sections 65, 70, and 75 of the stent pattern are subjected to substantial deformation as these portions bend during radial expansion and compression. Thus, these portions tend to be the most vulnerable to failure. The direction of stress in such portions is not necessarily aligned with the axial or circumferential directions.

Figure 3:
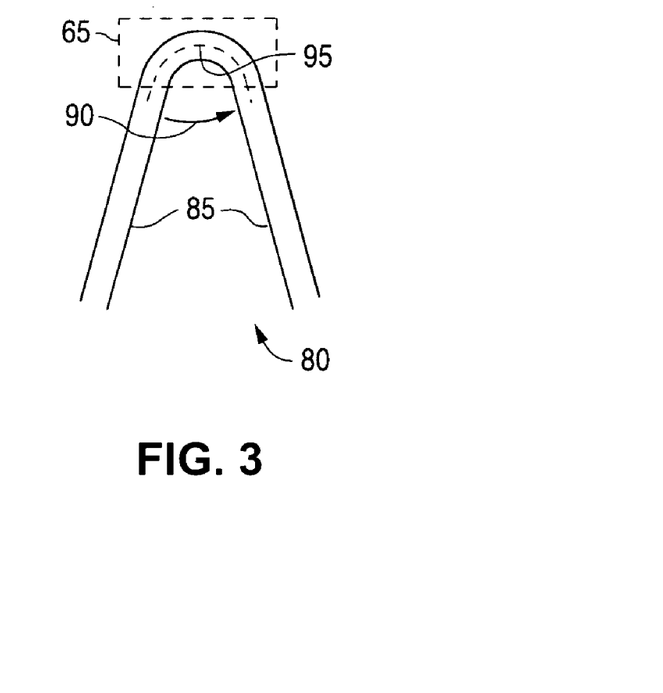
FIG. 3 depicts a bending portion of a stent pattern.
Figure 4:
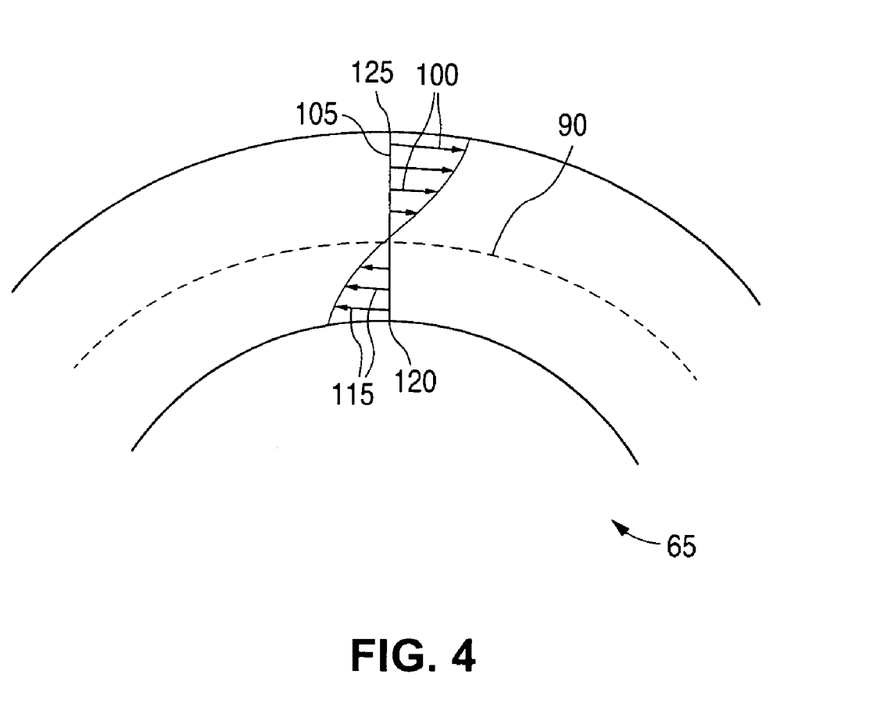
FIG. 4 depicts the magnitude of the strain as a function of the distance from a neutral axis in a bending portion of a stent.

FIGS. 3-4 illustrate the distribution of stress in structural elements of a stent. FIG. 3 depicts a portion 80 of a stent in a plane of bending. Radial expansion of a stent causes substantially no strain in straight sections 85. However, the bending of portion 80 results in relatively high stress and strain in curved section 65.

For example, when a stent is expanded, sections 85 move outward and angle 90 increases. The region above a neutral axis 95 experiences relatively high compressive stress and strain and the region below neutral axis 95 experiences relatively high tensile stress and strain. Alternatively, when a stent is crimped, sections 85 move inward and angle 90 decreases. The region above a neutral axis 95 experiences relatively high tensile stress and strain and the region below a neutral axis 95 experiences relatively high compressive stress and strain.

Furthermore, the strain in a structural element or beam increases with distance from the neutral axis. Therefore, the strain in section 65 depends on distance from the neutral axis 90 and the change in curvature from an equilibrium or unstressed curvature of section 65. FIG. 4 illustrates the magnitude of the strain as a function of the distance from neutral axis 90 in section 65 when a stent is crimped and angle 90 decreases. As indicated, above neutral axis 90 the strut is in tension with a tensile strain that increases with distance from neutral axis 90, as shown by arrows 110. Below neutral axis 90, the strut is in compression with a compressive strain that increases with distance from neutral axis 90, as shown by arrows 115. The maximum compressive or tensile strain along plane 105 is at edges 120 and 125, respectively.

Thus, the orientation of the direction of the stress and strain in structural elements of a stent with respect to a cylindrical axis can depend on the orientation of the bending portions. Furthermore, the direction of the compressive stress and strain may tend to approximately follow the curvature of the strut. Therefore, the direction of stress and stress also depends on the structure or shape of individual structural elements.

Due to the magnitude and directions of stresses imposed on an implantable medical device during use, it is important for the mechanical stability of a device to have an adequate magnitude of strength both in axial and circumferential directions. As illustrated by the exemplary stress distribution in a stent pattern in FIGS. 3 and 4, the direction of stress in structural members can be in various directions between axial and circumferential. Therefore, an adequate balance of axial and circumferential strength is also important for mechanical stability. The relative amount of axial and circumferential orientation may depend on a number of factors such as the stent pattern, initial diameter of the tube, final diameter of the stent, and crimped diameter of the stent.

Therefore, it is desirable to fabricate an implantable medical device from a polymeric tube with an adequate magnitude and balance of strength in the axial direction, as shown by an arrow 35 in FIG. 1 and in the circumferential direction as indicated by an arrow 40. A biaxial oriented tube may be configured to have adequate strength in both the circumferential and axial directions. Thus, for example, a stent made from a biaxially oriented tube may be less susceptible to cracking during crimping and deployment.

In addition, a biaxially oriented tube may allow a decrease in strut width, or generally, a decrease in form factor of a stent. Implantable medical devices, such as stents, fabricated from tubes with biaxial molecular orientation may possess mechanical properties similar to or better than metal stents with an acceptable wall thickness and strut width.

Polymer tubes may be formed by various types of methods, including, but not limited to extrusion or injection molding. A tube made from injection molding has a relatively low degree of polymer chain alignment in both the axial and circumferential directions. In extrusion, a polymer melt is conveyed through an extruder which is then formed into a tube. Extrusion tends to impart large forces on the molecules in the axial direction of the tube due to shear forces on the polymer melt. The shear forces arise from forcing the polymer melt through a die and pulling and forming the polymer melt into the small dimensions of a tube. As a result, polymer tubes formed by conventional extrusion methods tend to possess a significant degree of axial polymer chain alignment. However, such conventionally extruded tubes tend to possess no or substantially no polymer chain alignment in the circumferential direction.

As indicated previously, polymer chain alignment in conventionally fabricated tubes may be induced in the circumferential or both the circumferential and axial directions. Thus, the strength in either or both directions may be increased to a desirable level through such inducement. Additionally, a desired balance of axial and circumferential alignment, and thus strength, can also be induced. Circumferential and axial orientation in a tube may be induced through radial and axial deformation, respectively. The stress may be applied after fabrication of a tube by extrusion or injection molding, for example.

In some embodiments, a polymer tube may be deformed at a temperature below the $T_g$ of the polymer. Alternatively, it may be desirable to deform the tube in a temperature range greater than or equal to the $T_g$ of the polymer and less than or equal to the $T_m$ of the polymer. As indicated above, a polymeric material deforms much more readily due to segmental motion of polymer chains above $T_g$. Deformation induces polymer chain alignment that may occur due to the segmental motion of the polymer chains.

Therefore, heating the polymer tube prior to and/or contemporaneously with deformation may facilitate deformation particularly for polymers with a $T_g$ above an ambient temperature. Heating the tube contemporaneously with the deformation may be desirable since the deformation may occur at a constant or nearly constant temperature. Therefore, the induced polymer alignment and material properties may be constant or nearly constant.

In addition, oriented polymer chains tend to undergo relaxation when a polymer is above its $T_g$. Therefore, once stress is removed from a deformed polymer, it may be desirable to reduce its temperature to below its $T_g$ to retain the induced molecular orientation.

Various embodiments of fabricating an implantable medical device, such as a stent, are disclosed herein. The embodiments include fabricating a stent from a tube having a desired degree of both axial and circumferential strength.

In certain embodiments, a method of fabricating an implantable medical device may include radially deforming a polymeric tube about a cylindrical axis of the tube. Some embodiments may include deforming a polymer tube plastically beyond the yield point or elastic limit of the polymer. As indicated above, a polymer deformed beyond its yield point tends to retain its deformed configuration, and hence, tends to retain the induced molecular orientation. The radial deformation of the polymer tube may induce circumferential molecular orientation, and hence, increase the circumferential strength and modulus or rigidity in the polymer tube.

Additionally, the method may further include axially deforming the tube along the cylindrical axis. In one embodiment, the tube may be axially deformed by applying a tensile force to the tube along the cylindrical axis. In an embodiment, the tube may be axially deformed plastically beyond the yield point or elastic limit of the polymer. Axial deformation of the polymer tube may induce axial molecular orientation, and hence, increase the axial strength and modulus or rigidity. Various embodiments may include radially deforming the tube prior to, subsequent to, and/or contemporaneously with axial deformation the tube.

An implantable medical device may then be fabricated from the radially and axially deformed tube. Fabrication may include forming pattern of interconnecting structural elements or struts in the tube.

In general, the expansion and elongation of a tube are not independent. For instance, in one case, when a polymer tube is radially deformed or expanded in the absence of an axial tensile force, the axial length may tend to decrease. Similarly, in another case, when a polymer tube is axially deformed or elongated in the absence of a radial force, radial shrinkage may occur, i.e., the diameter of the tube may tend to decrease. In both cases, the thickness of the tube can decrease. Whether the radial thickness decreases or increases depends on the rate of deformation and the force applied to deform the tube. For example, a relatively high deformation rate and/or force can reduce radial thickness with less radial shrinkage. In addition, when the degree of radial deformation is higher than the degree of axial deformation, the radial thickness may tend to decrease. The degree of radial and axial deformation may be given by radial and axial draw ratios, respectively, which are defined below.

Some embodiments may include applying heat to the tube to facilitate radial and/or axial deformation of the tube. In some embodiments, the tube may be heated prior to, contemporaneously with, and/or subsequent to radially and axially deforming the tube.

As indicated above, it may be desirable to cool the deformed tube below the $T_g$ of the polymer to retain induced molecular orientation. Some embodiments may include cooling the radially and axially deformed tube prior to fabrication of the medical device. The deformed tube may be cooled at a temperature below an ambient temperature to below the $T_g$ of the polymer. Alternatively, cooling the deformed polymer tube may include cooling the deformed polymer tube at a temperature at or near an ambient temperature to below the $T_g$ of the polymer.

Certain embodiments may include radially and/or axially deforming the polymer tube at a temperature below a $T_g$ of the polymer. Other embodiments may include radially and/or axially deforming the polymer tube in a temperature range greater than or equal to a $T_g$ of the polymer and less than or equal to a $T_m$ of the polymer. As indicated above, a polymer is more easily deformed above its $T_g$. Below $T_m$, the polymer tube may retain its cylindrical shape even with applied pressure and tension.

In one embodiment, the tube may be deformed by blow molding. In some embodiments, a polymer tube for fabrication of an implantable medical device may be deformed radially by increasing a pressure in a polymer tube, for example, by conveying a fluid into the tube. The polymer tube may be deformed axially by applying a tensile force by a tension source at one end while holding the other end stationary. Alternatively, a tensile force may be applied at both ends of the tube.

In some embodiments, blow molding may include first positioning a tube in an annular member or mold. The mold may act to control the degree of radial deformation of the tube by limiting the deformation of the outside diameter or surface of the tube to the inside diameter of the mold. The inside diameter of the mold may correspond to a diameter less than or equal to a desired diameter of the polymer tube. Alternatively, the fluid temperature and pressure may be used to control the degree of radial deformation by limiting deformation of the inside diameter of the tube as an alternative to or in combination with using the mold.

As indicated above, the polymer tube may also be heated prior to, during, and subsequent to the deformation. In one embodiment, the tube may be heated by conveying a gas at a selected temperature on and/or into the tube. The gas may be the same gas used to increase the pressure in the tube. In another embodiment, the tube may be heated by translating a heating element or nozzle adjacent to the tube. In other embodiments, the tube may be heated by the mold. The mold may be heated, for example, by heating elements on, in, and/or adjacent to the mold.

Certain embodiments may include first sealing, blocking, or closing a polymer tube at a distal end. The end may be open in subsequent manufacturing steps. The fluid, (conventionally an inert gas such as air, nitrogen, oxygen, argon, etc.) may then be conveyed into a proximal end of the polymer tube to increase the pressure in the tube. The pressure of the fluid in the tube may act to radially deform the tube.

Additionally, the pressure inside the tube, the tension along the cylindrical axis of the tube, and the temperature of the tube may be maintained above ambient levels for a period of time to allow the polymer tube to be heat set. In one embodiment, the temperature of the deformed tube may be maintained at greater than or equal to the $T_g$ of the polymer and less than or equal to the $T_m$ of the polymer for a selected period to time. The selected period of time may be between about one minute and about two hours, or more narrowly, between about two minutes and about ten minutes.

"Heat setting" refers to allowing aligned polymer chains to equilibrate towards the induced highly oriented structure at an elevated temperature. Polymer chain alignment is a time and temperature dependent process. A highly oriented structure that is thermodynamically stable at a given temperature may not be formed instantaneously. Thus, the structure may be formed over a period of time. During this time period, the polymer in the deformed state may be maintained at an elevated temperature to allow polymer chains to adopt the highly oriented structure. The polymer may be maintained in the deformed state by maintaining a radial pressure and axial tension in the tube.

Alternatively, the polymer tube may be "heat shrunk" which refers to a decrease in the diameter and length of the tube. Pressure inside the tube and the tension may be allowed to decrease while maintaining the temperature of the tube above an ambient temperature prior to completion of heat setting. The polymer tube may be heat shrunk to a desired diameter and length.

In either heat setting or heat shrinking, the polymer tube may then be cooled to below its $T_g$ either before or after decreasing the pressure and/or decreasing tension. Cooling the tube helps insure that the tube maintains the proper shape, size, and length following its formation. Upon cooling, the deformed tube retains the length and shape imposed by an inner surface of the mold.

The degree of radial deformation may be quantified by a blow-up ratio or radial draw ratio:

$$\frac{\text{Outside Diameter of Deformed Tube}}{\text{Original Inside Diameter of Tube}}$$

In some embodiments, the radial draw ratio of a polymer tube for use in fabricating an implantable medical device may be between about 1 and 20, or more narrowly between about 2 and 6.

Similarly, the degree of axial deformation may be quantified by an axial draw ratio:

$$\frac{\text{Length of Deformed Tube}}{\text{Original Length of Tube}}$$

In some embodiments, the axial draw ratio of a polymer tube for use in fabricating an implantable medical device may be between about 0.5 and 20, or more narrowly between about 1 and 5.

In some embodiments, a tube may be radially and axially deformed to obtain a desired magnitude of radial and axial strength. Other embodiments may include, radially and axially deforming to obtain a desired ratio of circumferential strength to axial strength. Therefore, either or both a desired magnitude and ratio of radial and axial strength in the polymer tube may be achieved.

The radial and axial draw ratios necessary to obtain the desired magnitude and ratio of radial and axial strength may be determined in a variety ways. The radial and axial draw ratios may be found empirically either through experiment or modeling.

In one case, the desired radial and axial strengths and ratios may be known. To determine the required radial and axial draw ratio, conventionally fabricated tube may first be radially and axially deformed at different draw ratios and the radial and axial strengths may be measured. The measured strengths and ratios may then be compared to desired strengths and ratios.

In addition, desired strengths and ratios may be determined directly from a stent with a selected pattern. The mechanical behavior or performance of a stent with the selected pattern may be observed for different radial and axial draw ratios. The stents may be fabricated from deformed tubes with different radial and axial draw ratios. The mechanical behavior of the stent may be observed for both a crimped and deployed (expanded) state. Mechanical behavior may be observed using, for example, flat plate compression tests. The mechanical behavior that will be observed may include radial strength, recoil, crimped profile, and crack formation.

Additionally, modeling techniques such as finite element analysis may be employed. Draw ratios necessary to obtain a given radial and axial strength may be determined from such modeling techniques. Also, the mechanical behavior of stents with various radial and axial strengths and ratios may also be determined by modeling such stents.

As indicated above, the magnitude and direction of stress and strain in the structural elements of a stent pattern can depend on the orientation and shape of bending portions of the elements. Therefore, a stent pattern may require a desired range of strength along selected orientations. In some embodiments, the radial and axial draw ratio for a tube used for fabricating a stent may be selected to produce the desired range of strength along the selected orientations.

Figure 5:
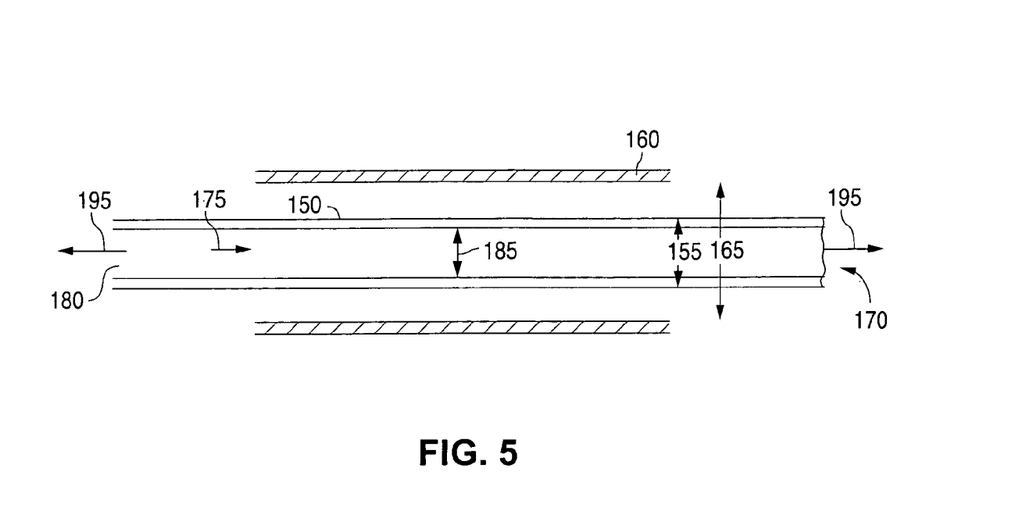
FIGS. 5-6 depict deformation of a polymer tube.
Figure 6:
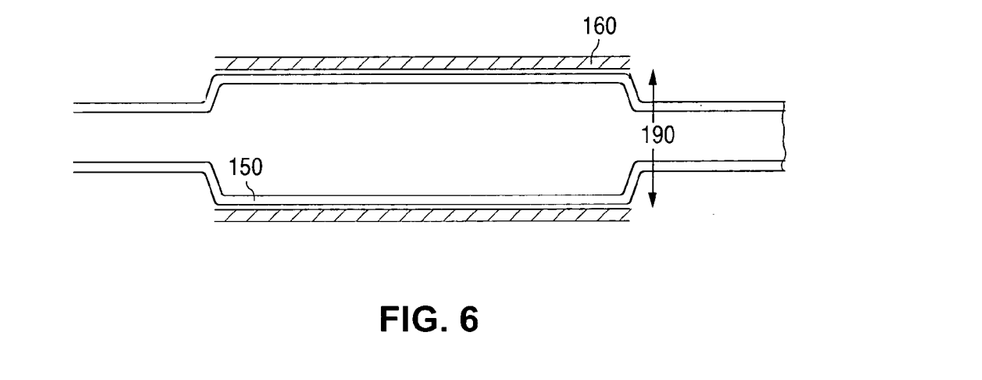

FIGS. 5 and 6 further illustrate an embodiment of deforming a polymer tube for use in manufacturing an implantable medical device, such as a stent. FIG. 5 depicts an axial cross-section of a polymer tube 150 with an outside diameter 155 positioned within an annular member or mold 160. Mold 160 may act to limit the radial deformation of polymer tube 150 to a diameter 165, the inside diameter of mold 160. Polymer tube 150 may be closed at a distal end 170. Distal end 170 may be open in subsequent manufacturing steps. A fluid may be conveyed, as indicated by an arrow 175, into an open proximal end 180 of polymer tube 150. A tensile force 195 is applied at proximal end 180 and a distal end 170.

Polymer tube 150 may be heated by heating the gas to a temperature above ambient temperature prior to conveying the gas into polymer tube 150. Alternatively, the polymer tube may be heated by heating the exterior of mold 160. The tube may also be heated by the mold. The increase in pressure inside of polymer tube 150, facilitated by an increase in temperature of the polymer tube, causes radial deformation of polymer tube 150, as indicated by an arrow 185. FIG. 6 depicts polymer tube 150 in a deformed state with an outside diameter 190 within annular member 160.

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

What is claimed is:

1. A method for fabricating a stent having increased strength, comprising:
    providing a first polymeric tube having a cylindrical axis;
    providing a stent pattern defining an orientation and shape of a bending portion of a stent strut relative to the cylindrical axis;
    applying a radial pressure and axial tension to the tube, including the steps of
        raising the temperature of the tube to above the glass transition temperature of the tube, and while at the raised temperature
        expanding the tube including simultaneously applying the axial tension and radial pressure to the tube according to a selected axial and radial draw ratio, respectively, wherein the axial and radial draw ratios are selected to cause polymer chains to align with the direction of stress and strain for the bending portion,
        after expanding the tube, cooling the tube to a temperature below the glass transition temperature while maintaining the applied pressure and tension to the tube; forming the stent from the deformed tube according to the stent pattern;
    crimping the stent to create a crimped state of the stent and then examining the stent's mechanical properties when in the crimped state;
    deploying the stent from the crimped state to a deployed state and then examining the stent's mechanical properties in the deployed state;
    selecting a new axial and radial draw ratio;
    providing a second polymeric tube having a cylindrical axis; and
    repeating the applying, forming, crimping and deploying step using the second tube and the new axial and radial draw ratio.

2. The method of claim 1, wherein the tube comprises a biostable and/or bioabsorbable polymer.

3. The method of claim 1, wherein the tube is deformed radially by applying a radial pressure.

4. The method of claim 3, wherein applying radial pressure comprises conveying a gas at a selected pressure into the tube.

5. The method of claim 1, wherein the tube is deformed axially by applying a tensile force along the cylindrical axis.

* * * * *